(12) United States Patent
Termanini

(10) Patent No.: US 7,172,565 B2
(45) Date of Patent: Feb. 6, 2007

(54) INTEGRATED ORTHOPEDIC BANDAGE SYSTEM AND METHOD FOR USING THE SAME

(75) Inventor: Zafer Termanini, Cedar Grove, NJ (US)

(73) Assignee: Beta Holdings, Inc., Parsippany, NJ (US)

( * ) Notice: Subject to any disclaimer, the term of this patent is extended or adjusted under 35 U.S.C. 154(b) by 0 days.

(21) Appl. No.: 10/825,936

(22) Filed: Apr. 16, 2004

(65) Prior Publication Data
US 2005/0182345 A1 Aug. 18, 2005

(30) Foreign Application Priority Data
Feb. 13, 2004 (KR) ............... 10-2004-0009721

(51) Int. Cl.
*A61F 5/00* (2006.01)
*A61F 13/00* (2006.01)
*A61F 15/00* (2006.01)

(52) U.S. Cl. ............. 602/8; 602/6; 602/5; 602/60
(58) Field of Classification Search ........... 602/6, 602/8; 206/441; 383/206; 442/76, 180; 428/294.7, 295
See application file for complete search history.

(56) References Cited

U.S. PATENT DOCUMENTS

| | | | | |
|---|---|---|---|---|
| 3,494,538 A | * | 2/1970 | Matthews | 206/481 |
| 3,521,745 A | | 7/1970 | Schwartzman | 206/47 |
| 3,656,475 A | | 4/1972 | Hanrahan, Jr. | 128/90 |
| 3,724,651 A | * | 4/1973 | Link | 206/363 |
| 3,797,493 A | * | 3/1974 | Saudek | 604/408 |
| 3,930,496 A | | 1/1976 | Gibbons | 128/90 |
| 3,990,437 A | | 11/1976 | Boyden, Jr. et al. | 128/90 |
| 4,019,506 A | | 4/1977 | Eschmann | 128/90 |
| 4,060,075 A | | 11/1977 | Blomer et al. | 128/90 |
| 4,131,114 A | | 12/1978 | Kirkpatrick et al. | 128/90 |
| 4,153,052 A | | 5/1979 | Tsuk | 128/90 |
| 4,331,134 A | | 5/1982 | Brooks et al. | 128/90 |
| 4,498,467 A | | 2/1985 | Kirkpatrick et al. | 128/90 |
| 4,537,184 A | * | 8/1985 | Williams, Jr. | 602/8 |
| 4,793,330 A | | 12/1988 | Honeycutt et al. | 128/90 |
| 4,899,738 A | * | 2/1990 | Parker | 602/8 |

(Continued)

OTHER PUBLICATIONS

MSN Encarta Dictionary: *LENGTH*, printed Mar. 29, 2006, 2 pages.*

(Continued)

*Primary Examiner*—Henry Bennett
*Assistant Examiner*—Kari Petrik
(74) *Attorney, Agent, or Firm*—Fitzpatrick, Cella, Harper & Scinto

(57) ABSTRACT

A water-curable orthopedic splint, which can be immediately applied to an affected limb includes a water-curable orthopedic casting material, which is in the form of a splint, and a gel container. The word gel is meant to apply to a viscous semi-solid which can be applied over surfaces in an adherent film and will disperse and move in response to the movement of the practitioner's hands in molding and forming the adhesive bandage around the limb or in the formation of various shapes as splints prior to application to the patient. It is to be distinguished from a free-flowing liquid which drips when applied to a limb resulting in a messy environment.

30 Claims, 3 Drawing Sheets

U.S. PATENT DOCUMENTS

| | | | |
|---|---|---|---|
| 4,928,678 A * | 5/1990 | Grim | 602/8 |
| 5,027,803 A | 7/1991 | Scholz et al. | 128/89 |
| 5,171,208 A | 12/1992 | Edenbaum et al. | 602/6 |
| 5,250,344 A | 10/1993 | Williamson et al. | 428/143 |
| 5,284,468 A * | 2/1994 | Nelson | 602/5 |
| 5,318,504 A * | 6/1994 | Edenbaum et al. | 602/8 |
| 5,476,440 A | 12/1995 | Edenbaum | 602/8 |
| 5,520,621 A * | 5/1996 | Edenbaum et al. | 602/8 |
| 5,713,838 A * | 2/1998 | Termanini | 602/8 |
| 6,007,504 A * | 12/1999 | Bailey et al. | 602/6 |
| 6,695,801 B1 * | 2/2004 | Toronto et al. | 602/6 |
| 2002/0161319 A1 * | 10/2002 | Matsumoto et al. | 602/8 |

OTHER PUBLICATIONS

MSN Encarta Dictionary: *LONGITUDINAL*, printed Mar. 29, 2006 2 pages.*

* cited by examiner

INTEGRATED ORTHOPEDIC BANDAGE SYSTEM AND METHOD FOR USING THE SAME

FIELD OF THE INVENTION

The present invention relates to a novel orthopedic splint including a self curing waterless material adapted to be applied to an injured limb, and a water-laden gel adapted to be applied to the splint material to cure the splint material.

BACKGROUND OF THE INVENTION

In the orthopedic field it is quite conventional to dip or soak water-curable casting materials into a supply of water to effect curing of the casting material. In the earlier days of the prior art, the cure was effected with plaster of Paris casts by soaking the plaster of Paris laden bandage in water and applying the thus laden bandage to the affected limb. However, this procedure was both messy and cumbersome, and required additional personnel to assist in application and clean-up.

In more recent times, the technology has advanced to the point where the plaster of Paris has been replaced with certain water-curable resins. The problem of water application, however, to cure the bandage has not been eliminated. It is still necessary to either soak the material in water, e.g. in a bucket or sink, and then mold the splint material before applying it to the affected limb. This technique still involves the cumbersome, messy technique of water immersion. Moreover, when the splint is applied to the surgical site or limb it presents a risk of infection since the water used to soak the material is nonsterile.

SUMMARY OF THE INVENTION

The present invention finds application to any water-curable casting material including fiberglass or polyester substrates impregnated with resins normally used in the orthopedic art. The invention also could be used with plaster of Paris splinting materials. It serves the purpose of eliminating the need for any extraneous supply of water other than the components supplied with the splinting material in an integrated form of an orthopedic splint or supplied separately in a kit with the splint. More specifically, the invention in its broadest concept relates to a water-curable orthopedic splint which can be immediately applied to an affected limb without water. However, a water-laden gel is either separately packaged or provided integral with the splint material. The word gel as used herein is meant to apply to a viscous semi-solid which can be applied over surfaces in an adherent film and will disperse and move in response to the movement of the practitioner's hands in molding and forming the adhesive splint on the limb. It is to be distinguished from a free-flowing liquid which when applied to a limb drips and causes the messy environment described above.

The invention is suitable for use with any orthopedic casting material that is water-curable. The gel can be any water-laden gel commonly employed in the medical or cosmetics industry or any other that is not so-employed, and is preferably an aqueous phase of the gel system. It also is preferably an emulsified vehicle incorporating the water as an essential ingredient. Water emulsions or gels prepared from water and well-recognized gel-forming materials such as polymers, thickeners and the like may be used. Materials such as hydroxymethyl cellulose, hydroxypropyl cellulose, mixtures thereof, acrylates, polyglycols, such as polypropylene glycol, and the like are suitable. The gel may also contain hardeners and accelerators for the curing such as tertiary amines, methylethylketone peroxide and diethylether, respectively and catalysts therefor including copper salts and other art-known materials.

A suitable kit for carrying out the process of the present invention is a packaged set containing the orthopedic splint material which may consist of one or more layers of fiberglass or polyester sheets. The kit also includes a packaged water-laden gel system. In this preferred embodiment, the gel may be supplied in a squeezable pouch or package such as those used for condiments. The pouch is an air and water tight sealed foil container formed of aluminum foil or plastic. The pouch is supplied within the package with the splint material, a device useful for tearing the gel containing pouch is also provided. This can be a pull thread or string which, when pulled, will rupture the side of the pouch. The water-laden gel will then come in fluid communication with the orthopedic splint material, thereby allowing the resin to cure. The gel in the container is expelled after opening of the pouch by simply pressing and kneading the container to direct the gel contents thereof into the orthopedic splint material. This is preferably done immediately prior to removal of the splint material from the outer package. This avoids the prior art technique of removing the orthopedic bandage and dipping it in water before applying it onto the patient.

Two distinct packages or containers have been mentioned above in connection with various embodiments of the invention. The first is the outer package for the splint material. The normal packaging currently used in the art for supplying orthopedic casting material may be used in the invention as well. Typically, these are the foil type packages which are sealed against outside moisture and air. In general, any such packaging used in the art for such purpose is also suitable for use in the invention.

BRIEF DESCRIPTION OF THE DRAWINGS

The invention and certain embodiments thereof will be better understood from a consideration of the figures in which.

DETAILED DESCRIPTION OF THE INVENTION

Figure 1:
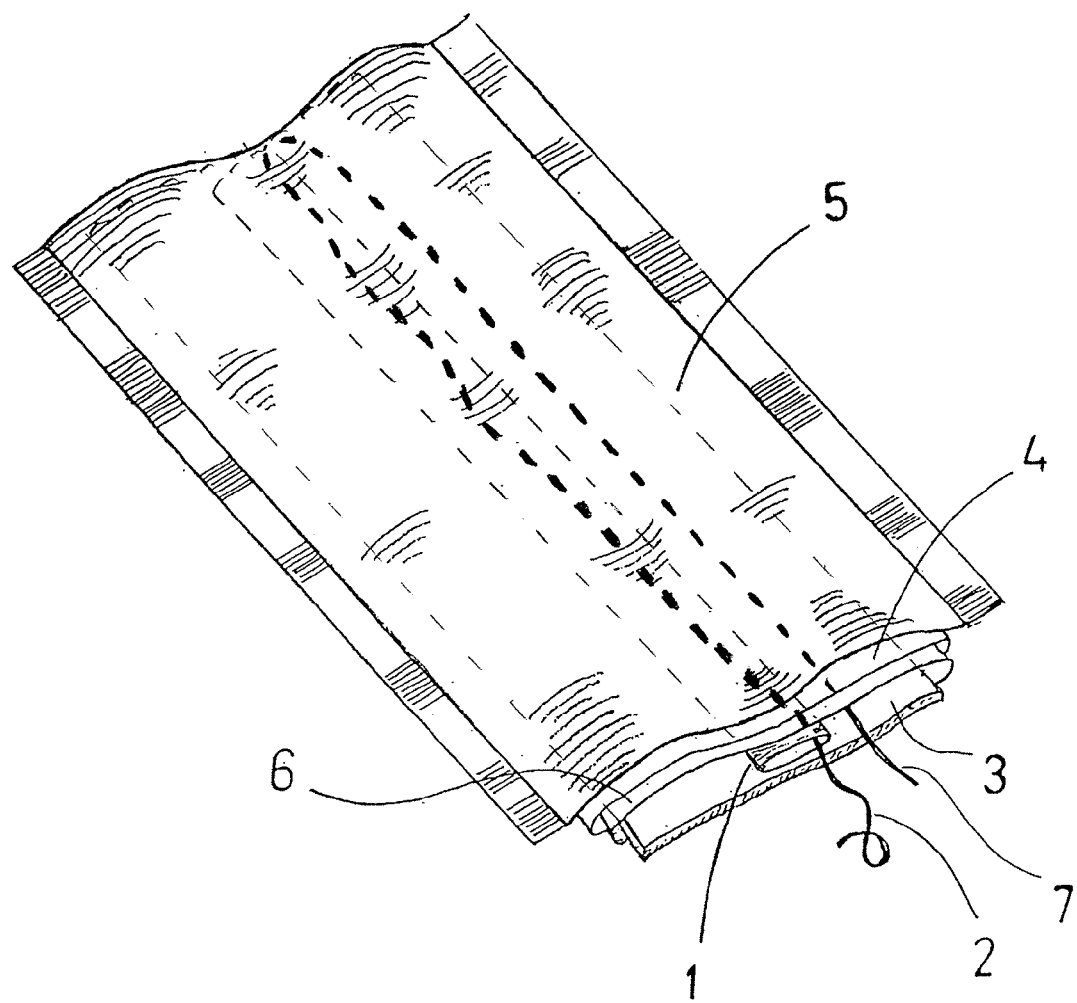
FIG. 1 is a perspective view of an embodiment of the invention showing the outer package opened at one end and the inner components broken away to illustrate the contents of the package.
Figure 2:
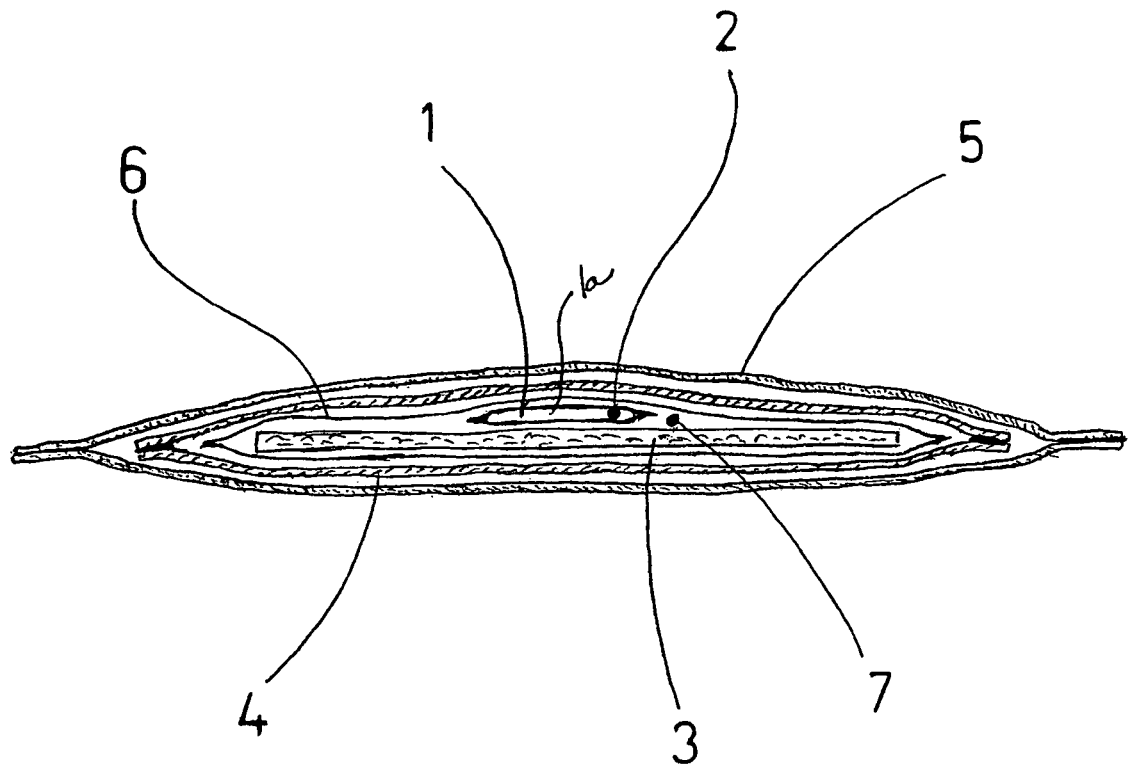
FIG. 2 is a cross sectional view of the package shown in FIG. 1.

A greater appreciation for an embodiment of the invention will be gained by reference to FIG. 1 wherein a curable casting material 3 is shown supplied as a flat sheet or sheets contained in package 5. The package also includes an inner padding sleeve 4 which surrounds the sheets 3. A further water tight inner membrane or sleeve is located inside the padding sleeve 4 and surrounds the sheets 3. Finally, an air and water tight pouch 1 is provided containing the water laden gel 1a. The pouch is located within membrane 6 in contact with sheets 3 and may have substantially the same length dimension as those sheets.

In use, the orthopedic surgeon removes the padding sleeve 4 containing the membrane 6, sheets 3 and pouch 1 from the outer aluminum foil type package 5. At this point, there is no need for the use of any water or other material to be applied to the casting material.

Figure 3:
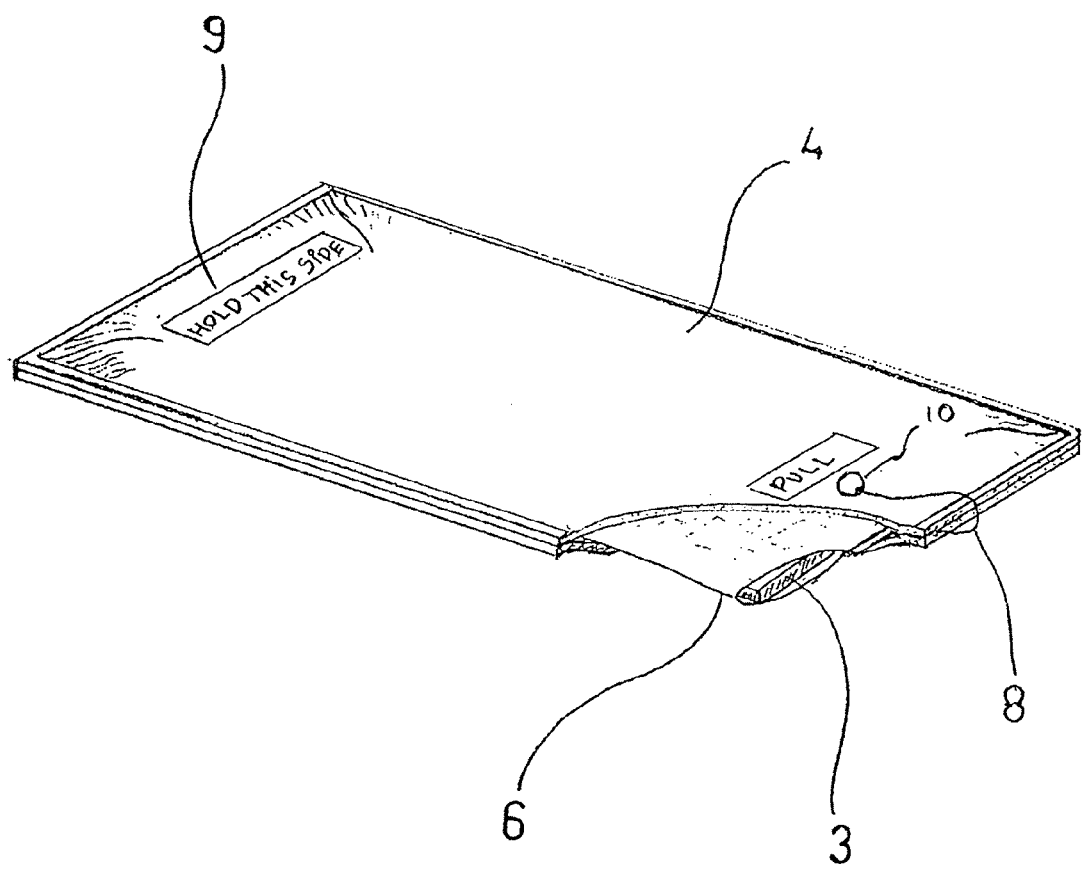
FIG. 3 is a perspective view of another embodiment of the invention.

As seen in FIG. 1, a tear string 7 is provided having one end 2 secured inside the pouch 1 in any convenient manner. The string 7 extends the length of the pouch, exits the pouch through a gel-tight seal at the opposite end of the pouch from that containing end 2 and is folded so that its tag end 8 is located outside pouch 1, extending through membrane 6 and padding 4. By this construction the surgeon may simply grasp the ends 9 of the padding 4 (see FIG. 3), membrane and splint material and pull the tag end 8 of string 7 (which may have a pull ring 10 or tag thereon). This will cause the string in pouch 1 to tear open the side of the pouch allowing the gel to escape and come into contact with the splint material 3. This process may be facilitated by the surgeon's hands and fingers kneading the gel over the entire surface of the sheet material. The gel will be contained by the water tight membrane 6 so that it contacts only sheets 3 and does not contact the padding sleeve 4, thereby assuring that the padding remains dry and, when the splint is applied to the patient's limb, only the dry padding contacts the limb, thereby avoiding problems of infection and itching.

The splint then cures as it normally would without the normal cumbersome application and water-soaking technique required in the art. The expedient of having the water-laden gel either integrally associated with the splint material in a water tight membrane within the sterile sleeve provides a speedy simple application and curing technique that requires no unusual clean-up activities.

The sheet material 3 is preferably a water-curable casting material such as fiberglass or weaved synthetic fabric (such as polyester) impregnated with a water-curable resin such as a polyurethane illustrated by those obtained from arylalkane diisocyanates, and especially diphenylmethane diisocyanate. In this particular embodiment, the outer package 5 preferably is a protective aluminum foil type of pouch normally used in the art. As noted above, the foil pouch is shown open for purposes of clarity.

Pouch 1 is shown in contact with the orthopedic splint material 3 and may be anchored to either the sheets 3 or the membrane 6 so that when the opening means or thread 7 is pulled, pouch 1 will remain relatively stationary. Of course, there also may be some degree of adhesion of pouch 1 to the orthopedic splint material in view of the normally tacky nature of many orthopedic water-curable resin materials. Instead of having the opening means being the thread 7, pouch 1 can be made of a material which can be ruptured upon impact (as by exerting force on the container when it is desired to release the gel) and thereby release the gel into the immediate environment of the orthopedic bandage.

The orthopedic surgeon also has the option of opening the package 5 and removing the casting material and applying the splint on an appropriately protected limb without having released the gel from pouch 1. Once the casting material has been applied and the pouch 1 has been opened, the surgeon can then eject the gel from the pouch by squeezing on it as one might from a tube of toothpaste or foil condiment package. Of course, it goes without saying that one must be cognizant of the curing effect once the gel meets the water-curable system and must proceed with appropriate haste.

As water-curable orthopedic materials there may be mentioned polymers or pre-polymers such as those described in U.S. Pat. Nos. 3,630,194, 4,344,423, 4,871,845, 5,476,440, and 5,713,838 but any water-curable materials may be used.

As water-laden gels for use in the present invention virtually any material which can be supplied in a gel-like phase is suitable provided it contains an adequate supply of releasable water. Materials such as gels or gelling materials such as propylene glycol, polypropylene glycol, hydroxypropyl, and hydroxymethyl cellulose, starch, thickeners, and the like may be employed.

The amount of water present in the gel is not critical except to the extent that one wishes to have enough water in the available volume of gel space to provide adequate curing once applied to the bandage system. Gel systems containing too much water, while operative are preferably avoided in order to minimize the amount of free-flowing water and therefore any attendant potential messy situation that requires clean-up. Gels containing too little water are preferably avoided so as to eliminate the need for using large amounts thereof.

There has thus been described a method of curing a water-curable orthopedic splint and a device and kit for so doing without the need for extraneous amounts of free-flowing water as in the prior art resulting in a simple rapid easily manipulated cast application system.

The invention claimed is:

1. An integrated orthopedic bandage system comprising:
   a) a water-curable orthopedic casting material, which is in the form of a splint and has both length and width dimensions, with the length dimension being longer than the width dimension; and
   b) a container including water which is removable from said container, said container having substantially the same length dimension as that of said casting material.

2. The system of claim 1 wherein said container includes water-laden gel containing the water and is in fluid communication with said orthopedic casting material.

3. The system of claim 2 wherein the gel comprises a member selected from the group consisting of hydroxymethyl cellulose, hydroxypropyl cellulose, acrylates, polyglycols, and propylene glycol.

4. The system of claim 3 wherein there is present in the gel a material selected from the group consisting of hardeners and accelerators.

5. The system of claim 1 wherein said casting material is in a flat arrangement.

6. The system of claim 1 wherein said container is provided with opening means operable to permit the release of the water therefrom into contact with said orthopedic casting material.

7. The system of claim 6 wherein said container comprises a rupturable flat long pouch and the opening means is a string which extends along said container so that when pulled the string ruptures said container to expose the gel contained in said container to said casting material.

8. The system of claim 1 wherein said orthopedic casting material is protected with a protective sleeve.

9. The system of claim 8 wherein said container is anchored to said sleeve.

10. The system of claim 9 wherein there is some degree of adhesion of said container to said casting material.

11. The system of claim 8 wherein said protective sleeve is water-resistant.

12. The system of claim 11 wherein said protective sleeve is contained within a padding sleeve.

13. The system of claim 1 further comprising an outer package which encloses said water-curable orthopedic casting material and said container.

14. The system of claim 1 wherein said orthopedic casting material comprises fiberglass, or weaved synthetic fabric.

15. The system of claim 14 wherein said orthopedic casting material includes a water-curable resin.

16. The system of claim 15 wherein the water-curable resin is polyurethane.

17. A method for curing a water-curable orthopedic casting material, which is in the form of a splint and has both length and width dimensions, with the length dimension being longer than the width dimension, the method comprising applying to an orthopedic material to be cured, an effective amount of water,
wherein the orthopedic casting material and the water are present in a package wherein the water is provided in a container from which it is removable into fluid communication with the casting material whereby when the water is removed from the container, the water directly contacts the casting material substantially along the entire length dimension of the casting material.

18. The method of claim 17 wherein the water is in the form of a water-laden gel.

19. The method of claim 18 wherein the gel comprises a member selected from the group consisting of hydroxymethyl cellulose, hydroxypropyl cellulose, acrylates, polyglycols, and propylene glycol.

20. The method of claim 17, wherein the container comprises a rupturable flat long pouch and said applying step comprises manipulating a string which extends along the surface of the container or is located inside the container in the longitudinal direction of the container so that when pulled it ruptures the container to expose the water contained in the container to the casting material.

21. The method of claim 17 wherein the orthopedic casting material is protected with a protective sleeve.

22. An integrated orthopedic bandage system comprising:
a) a water-curable orthopedic casting material, which is in the form of a splint;
b) a container including water which is removable from said container and having longitudinal and transverse dimensions with the longitudinal dimension being larger than the transverse direction; and
c) opening means for opening said container, said opening means positioned relative to said container so that when pulled said opening means ruptures said container substantially along its longitudinal dimension to expose the water contained in said container to said casting material.

23. The system of claim 22 wherein said opening means comprises a string extending substantially along the longitudinal dimension of said container.

24. The system of claim 22 wherein said container includes water-laden gel containing the water and is in fluid communication with said orthopedic casting material.

25. The system of claim 24 wherein the gel comprises a member selected from the group consisting of hydroxymethyl cellulose, hydroxypropyl cellulose, acrylates, polyglycols, and propylene glycol.

26. The system of claim 24 wherein there is present in the gel a material selected from the group consisting of hardeners and accelerators.

27. The system of claim 22 wherein said casting material is in a flat arrangement.

28. The system of claim 22 wherein said orthopedic casting material is protected with a protective sleeve.

29. The system of claim 28 wherein said container is anchored to said sleeve.

30. The system of claim 29 wherein there is some degree of adhesion of said container to said casting material.

* * * * *